(12) United States Patent
Ittel et al.

(10) Patent No.: US 7,816,467 B2
(45) Date of Patent: Oct. 19, 2010

(54) PROCESSES FOR HYDRAZINE ADDITION TO ACRYLIC MACROMONOMERS AND PRODUCTS THEREFROM

(75) Inventors: Steven Dale Ittel, Wilmington, DE (US); Alexei A. Gridnev, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 817 days.

(21) Appl. No.: 11/609,629

(22) Filed: Dec. 12, 2006

(65) Prior Publication Data

US 2007/0161675 A1 Jul. 12, 2007

Related U.S. Application Data

(60) Provisional application No. 60/751,475, filed on Dec. 16, 2005.

(51) Int. Cl.
| | |
|---|---|
| *C08F 4/04* | (2006.01) |
| *C08F 2/00* | (2006.01) |
| *C08F 126/02* | (2006.01) |
| *C08F 20/00* | (2006.01) |
| *C08F 20/52* | (2006.01) |
| *C08K 5/34* | (2006.01) |
| *C08K 3/28* | (2006.01) |

(52) U.S. Cl. ............ 526/218.1; 526/219.1; 526/301; 526/303; 526/310; 524/99; 524/428

(58) Field of Classification Search ............ 526/194, 526/204, 201, 206, 209, 213, 215, 217, 310, 526/304, 306, 217.1, 218.1, 219.1, 301, 303; 525/330.3, 509; 524/99, 428, 612
See application file for complete search history.

(56) References Cited

U.S. PATENT DOCUMENTS

| | | | |
|---|---|---|---|
| 4,680,352 A | 7/1987 | Janowicz et al. | |
| 4,694,054 A | 9/1987 | Janowicz | |
| 4,886,861 A | 12/1989 | Janowicz | |
| 5,028,677 A | 7/1991 | Janowicz | |
| 5,264,530 A * | 11/1993 | Darmon et al. | ............ 526/194 |
| 5,587,431 A | 12/1996 | Gridnev et al. | |
| 5,773,534 A | 6/1998 | Antonelli et al. | |
| 5,883,206 A | 3/1999 | Ittel et al. | |
| 6,117,958 A | 9/2000 | Ittel et al. | |
| 6,388,036 B1 | 5/2002 | Gridnev et al. | |
| 6,624,261 B1 | 9/2003 | Moad et al. | |

FOREIGN PATENT DOCUMENTS

RU     2169156    *   5/2001

OTHER PUBLICATIONS

Y. Brun, The Mechanism of Copolymer Retention Interaction Polymer Chromatography, J. Liq. Chrom. & Rel. Techniques, 1999, vol. 22:3027-3065.

Y. Brun et al., Gradient Separation of Polymers at Critical Point of Adsorption, J. Chromatography A, 2002, vol. 966:25-40.

* cited by examiner

*Primary Examiner*—Ling-Siu Choi
*Assistant Examiner*—Monique Peets

(57) ABSTRACT

Processes for forming adducts of hydrazines with acrylic macromonomers are provided. Also provided are processes for using ring-closing reactions of the adducts to form aminolactams. The adducts are useful, for example, for making adhesives, surfactants, viscosity modifiers, processing aids, and other products.

6 Claims, No Drawings

PROCESSES FOR HYDRAZINE ADDITION TO ACRYLIC MACROMONOMERS AND PRODUCTS THEREFROM

FIELD OF THE INVENTION

The present invention relates to adducts of hydrazines with acrylic oligomers and macromonomers and processes for forming the adducts. The invention further relates to processes for forming aminolactams using ring-closing reactions of the adducts.

BACKGROUND

Block copolymers and functionalized macromonomers are essential components of modern dispersants, inks, and paints. They are also utilized in a variety of other applications such as dispersants, crosslinkers, curing agents, stain resists, resists, compatibilizers, and surfactants, to name just a few applications. There is always a need for new block copolymers and functionalized macromonomers with new physical and chemical properties.

Cobalt-catalyzed chain transfer (CCT) in free radical oligomerizations or polymerizations of acrylics is a well established, commercial technology. The CCT process produces terminally unsaturated macromonomers and the technology is compatible with a wide range of functionalities.

Hydrazine and organohydrazines are very reactive and highly functional molecules. A reaction that combines the range of available CCT macromonomers with the high functionality of hydrazines would be a powerful tool for the design of new macromonomers and block copolymers for a variety of applications.

SUMMARY OF THE INVENTION

One aspect of the present invention is a composition having the structure

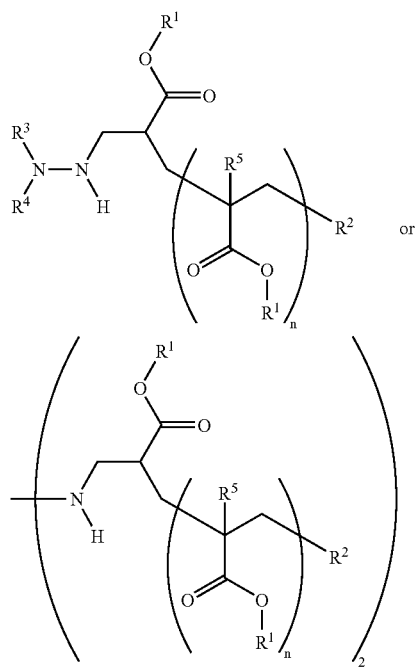

-continued

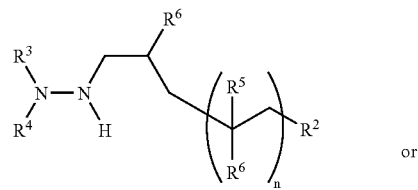

or

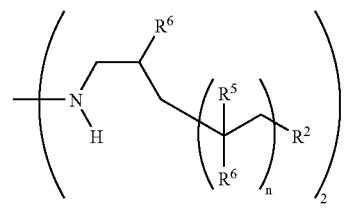

wherein each $R^1$ and $R^2$ are independently H, alkyl of 1-20 carbon atoms, aryl, substituted alkyl of 1-20 carbon atoms, or substituted aryl; $R^3$ and $R^4$ are independently H, alkyl of 1-100 carbon atoms, or substituted alkyl of 1-100 non-hydrogen atoms; $R^5$ is methyl, hydrogen or hydroxymethyl; n=1-100; and $R^6$ are independently —CN, —CO$_2$R$^1$, —COR$^1$, or —CONR$^1$R$^1$.

Another aspect of the present invention is a composition having the structure

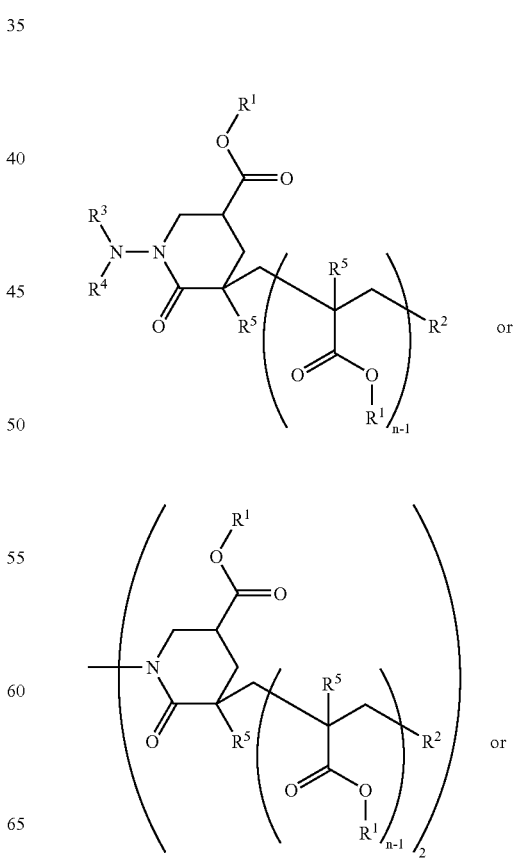

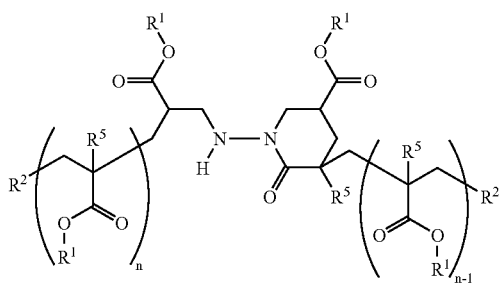

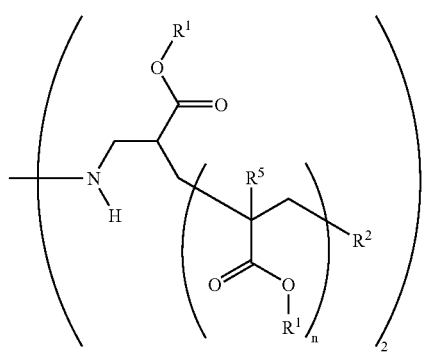

wherein $R^1$ and $R^2$ are independently H, alkyl of 1-20 carbon atoms, aryl, substituted alkyl of 1-20 carbon atoms, or substituted aryl; $R^3$ is H, alkyl of 1-100 carbon atoms, or substituted alkyl; $R^5$ is methyl, hydrogen or hydroxymethyl; and n=1-100.

A further aspect of the present invention is a composition having the structure

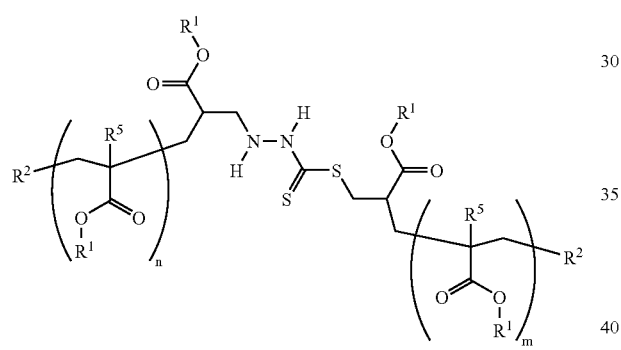

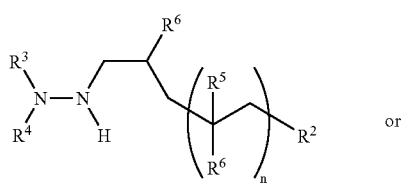

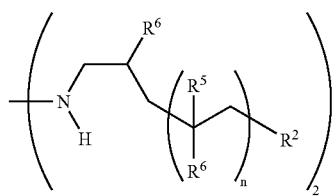

wherein $R^1$ and $R^2$ are independently H, alkyl of 1-20 carbon atoms, aryl, substituted alkyl of 1-20 carbon atoms, or substituted aryl; $R^5$ is methyl, hydrogen or hydroxymethyl; n=1-100 and m=0-100.

Another aspect of the present invention is a process of synthesizing a compound having a formula of:

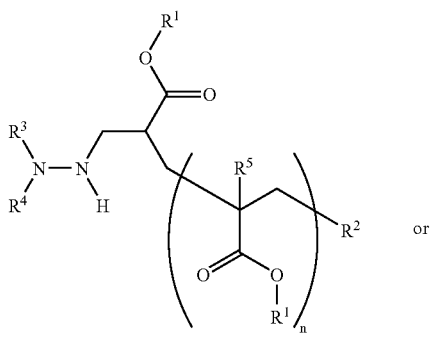

comprising contacting a hydrazine with a macromonomer of formula

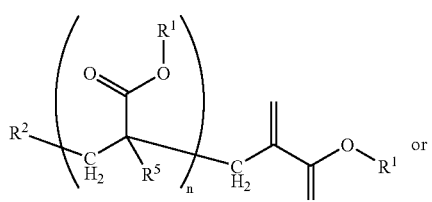

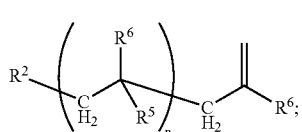

wherein $R^1$ and $R^2$ are independently H, alkyl of 1-20 carbon atoms, aryl, substituted alkyl of 1-20 non-hydrogen atoms, or substituted aryl; $R^3$ and $R^4$ are independently H, alkyl of 1-20 carbon atoms, or substituted alkyl of 1-20 non-hydrogen atoms; $R^5$ is methyl, hydrogen or hydroxymethyl; n=1-100, and $R^6$ are independently —CN, —$CO_2R^1$, —$COR^1$, or —$CONR^1R^1$.

A further aspect of the present invention is a process of synthesizing a compound of formula:

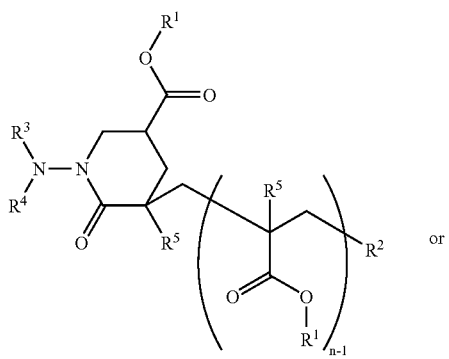
or
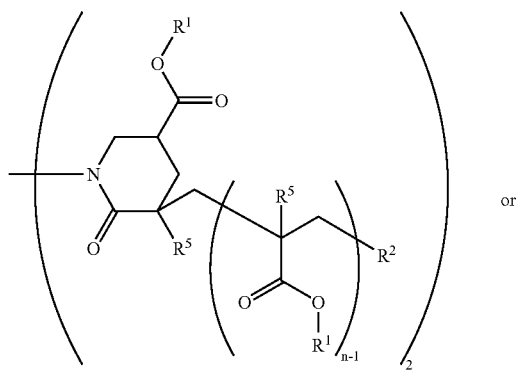
or

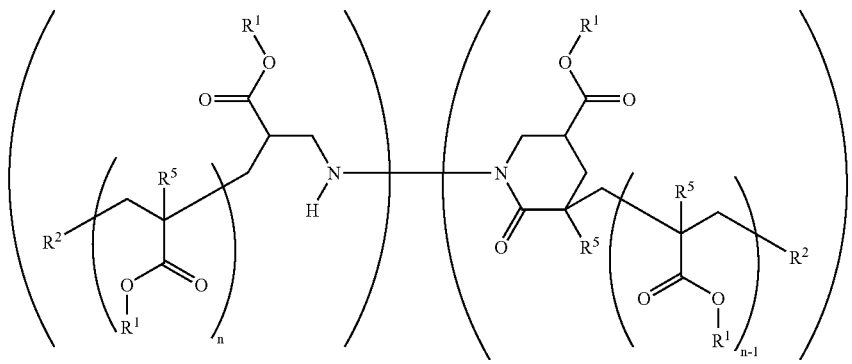

comprising contacting a hydrazine with a macromonomer of formula

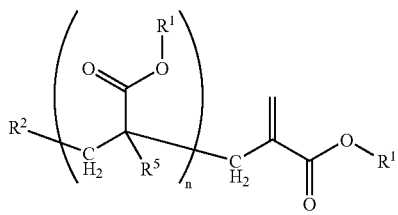

wherein $R^1$ and $R^2$ are independently H, alkyl of 1-20 carbon atoms, aryl, substituted alkyl of 1-20 nonhydrogen atoms, or substituted aryl; $R^3$ are independently H, alkyl of 1-20 carbon atoms, substituted alkyl of 1-20 non-hydrogen atoms; $R^5$ is methyl, hydrogen or hydroxymethyl; and n=1-100.

Another aspect of the present invention is a process of synthesizing a compound having a formula of:

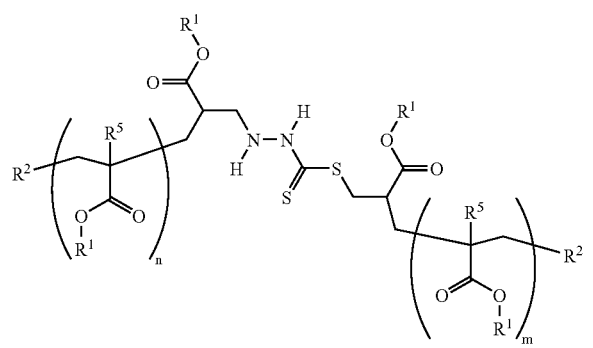

comprising contacting a hydrazine adduct of a macromonomer,

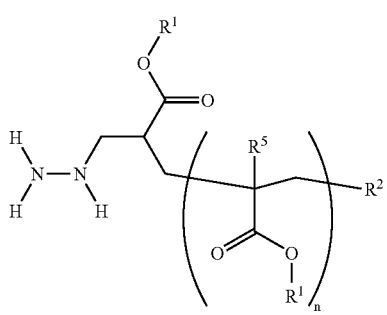

with a macromonomer of formula

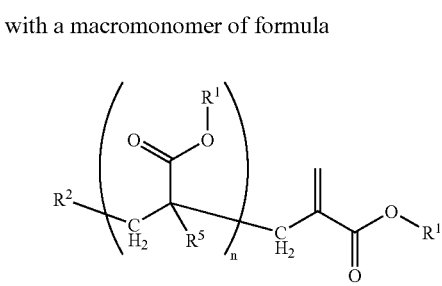

in the presence of carbon disulfide;

wherein $R^1$ and $R^2$ are independently H, alkyl of 1-20 carbon atoms, aryl, substituted alkyl of 1-20 non-hydrogen atoms, or substituted aryl; $R^3$ and $R^4$ are independently H, alkyl of 1-20 carbon atoms, or substituted alkyl of 1-20 non-hydrogen atoms; $R^5$ is methyl, hydrogen or hydroxymethyl; n=1-100, and $R^6$ are independently —CN, —$CO_2R^1$, —$COR^1$, or —$CONR^1R^1$.

These and other aspects of the present invention will be apparent to one skilled in the art in view of the following description and the appended claims.

DETAILED DESCRIPTION

One embodiment of the present invention includes the addition of hydrazine or organohydrazine compounds

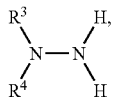

to macromonomers prepared by cobalt-catalyzed chain transfer and having terminal olefinic functionality to yield products having the structure

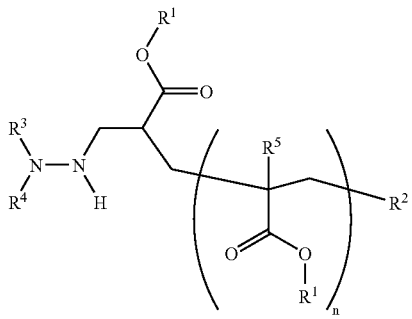

wherein $R^3$ and $R^4$ are independently H, alkyl of 1-100 carbon atoms, or substituted alkyl of 1-100 non-hydrogen atoms and $R^3$ and $R^4$ may be connected in a cyclic structure; each $R^1$ is independently H, alkyl of 1-20 carbon atoms, aryl, substituted alkyl of 1-20 carbon atoms, or substituted aryl; $R^5$ is methyl, hydrogen or hydroxymethyl; and n=1-100. It is preferred that $R^3$ and $R^4$ be chosen from hydrogen and alkyls ranging from methyl to dodecyl; preferred $R^1$ groups include methyl, ethyl, propyl, butyl, hexyl octyl, dodecyl, hydroxymethyl, and benzyl, H, alkyl of 1-20 carbon atoms, aryl, substituted alkyl of 1-20 carbon atoms, or substituted aryl; preferred $R^5$ group is methyl; and preferred n=1-20.

In some embodiments, a process includes subjecting compounds of formula to a ring-closing step, forming compounds having the structures

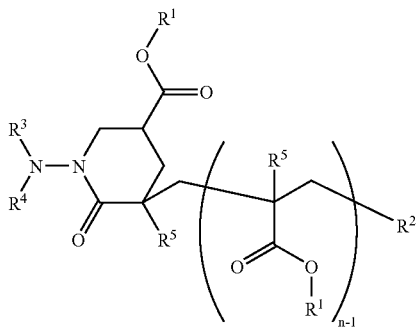

wherein the $R^3R^4N$—N portion of the molecule is derived from the reacting hydrazine and the remainder of the structure is derived from the CCT macromonomer. When the hydrazine chosen for the reaction is unsubstituted, a hydrazine-functionalized macromonomer results. That amino-functionalized macromonomer can be reacted with more of the same macromonomer or with a new macromonomer to yield the dimeric species that may be represented by

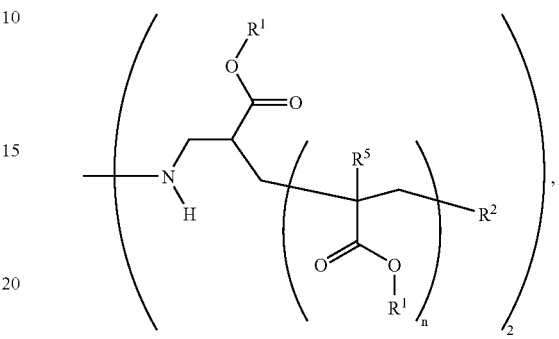

for a simple double addition to the hydrazine

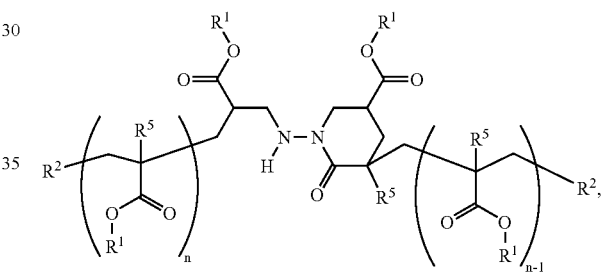

for a more complex addition product in which one of the hydrazine nitrogen atoms has formed a cyclized product while the other has not, and finally

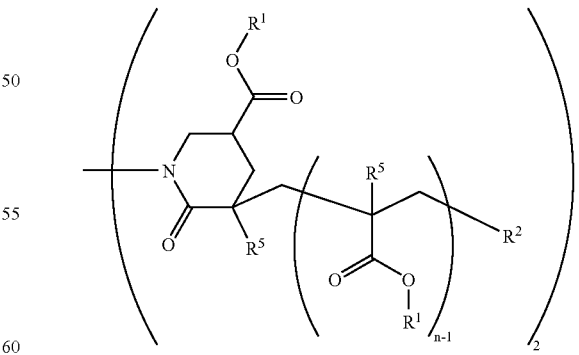

the product in which both of the hydrazine nitrogen atoms have formed cyclized products. The composition of the product is dependent upon the conditions employed, with higher temperatures favoring the formation of cyclized species. When the reaction is carried out in the presence of carbon disulfide with non-cyclized mono-adduct, the product

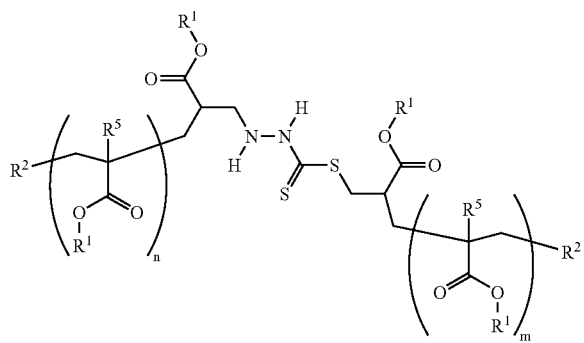

is obtained.

The processes shown in the following structures include reactions with R³-containing molecules having more than one reactive amino group. As an illustrative example of one embodiment, if the reaction is limited to monofunctional primary hydrazines, then the reaction can be represented by the addition

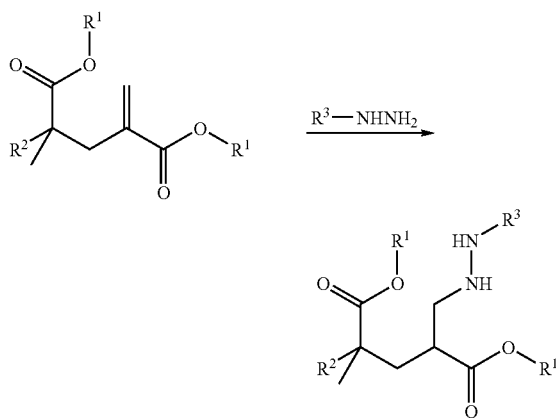

The hydrogen atom on the added hydrazine nitrogen is reactive and under more vigorous conditions the reaction may proceed further, going through a ring-closing reaction

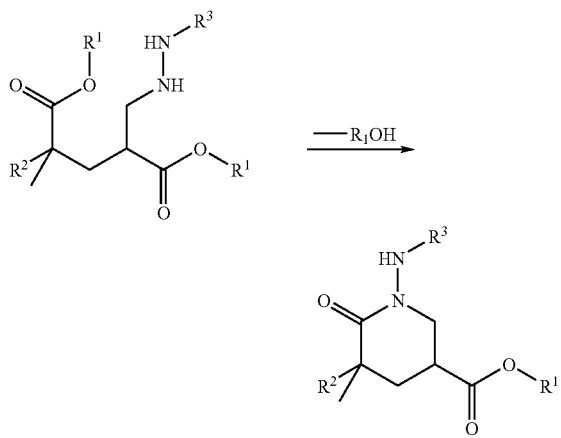

Cobalt-catalyzed chain transfer (CCT) in free radical oligomerizations or polymerizations of acrylics is a well established, commercial technology. The CCT process produces terminally unsaturated macromonomers and the technology is compatible with a wide range of functionalities. Catalytic chain transfer is particularly useful in the polymerization or oligomerization of methacrylates where it yields compounds having the structure

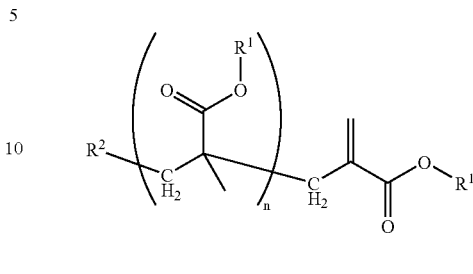

wherein each $R^1$ and $R^2$ are independently H, alkyl of 1-20 carbon atoms, aryl, substituted alkyl of 1-20 carbon atoms, or substituted aryl and $R^5$ is methyl, hydrogen or hydroxymethyl, and n=1-100, preferably n=1-50. These and related species are referred to herein interchangeably as "oligomers," or "macromonomers" and the terms are further intended to incorporate the products of copolymerizations of methacrylates with other methacrylates as well as with acrylates and with other free-radically copolymerizable monomers. These oligomers and their production are described in a series of U.S. patents issued to DuPont that include U.S. Pat. Nos. 6,624,261, 6,388,036, 6,117,958, 5,883,206, 5,587,431, 5,028,677, 4,886,861, 4,694,054, and 4,680,352. While there is no intent to limit the molecular weight of the oligomers useful in this invention, they will generally range from dimers (n=1) to species in which n may be hundreds. Most frequently, n will range from 1 to 20.

As used herein, the term "acrylic" is a general term meant to encompass a variety of ethylenically unsaturated monomers and comonomers that may be copolymerized with methacrylate monomers to form the oligomers or macromonomers employed in this disclosure. Thus the resulting macromonomers may comprise a variety of methacrylate ester monomers, acrylate ester monomers, styrene and alpha-methylstyrene, acrylonitrile and methacrylonitrile monomers. Other comonomers such as methylenebutyrolactone, vinylpyrrolidinone, chloroprene, vinyl acetate may also be incorporated into the macromonomers in lesser amounts.

The substituent $R^1$ on the ester group is selected from alkyl or substituted alkyl groups, aryl groups, and substituted aryl groups. The terminal substituent, $R^2$, on the ester group is selected from hydrogen atom; alkyl substituted alkyl aryl and substituted aryl.

By "alkyl" is meant a linear or branched saturated hydrocarbyl unit ranging from methyl, ethyl, propyl, to much higher carbon numbers including polymeric species. Branched alkyl includes isopropyl, isobutyl, sec-butyl, neopentyl, and much higher carbon numbers including polymeric species.

A "substituted alkyl" is an alkyl having a non-hydrogen functionality attached to or in place of any of the carbon atoms of the alkyl. The substituents may be the same or different and selected, for example, from carboxylic ester, hydroxyl, alkoxy, tertiary amino, trifluoromethyl, perfluoroalkyl and other substituted and unsubstituted alkyl, substituted and unsubstituted aryl, substituted and unsubstituted olefin and halogen. Substituted alkyl also includes species in which one or more of the carbon atoms other than the first carbon atom of the alkyl are substituted with heteroatoms such as oxygen, sulfur, silicon, tin or other elements. Substituted alkyl groups generally do not bear functionality that can react with hydrazines under the conditions of the reactions disclosed herein. If such reactions can occur, they are taken into consideration when formulating a stoichiometry for the reaction. For instance, a glycidyl group would be an inappropriate choice of substituted alkyl because it is well known to those skilled in the art that hydrazines will cause a ring-opening reaction of the epoxy functionality. Carboxylic acids will react with the hydrazines to form hydrazonium salts thereby inhibiting the reaction.

Preferred alkyl or substituted alkyl groups include methyl, ethyl, propyls (all isomers), butyls (all isomers), 2-ethylhexyl, isobornyl, octyl (all isomers), higher normal and branched alkyls, and cyclohexyl. Benzyl and substituted benzyls, neophyl, phenylethyl, and naphthylmethyl are preferred examples of arylalkyls, a class of substituted alkyls. Preferred examples of substituted alkyl groups include 2-hydroxyethyl, 2-hydroxypropyl, trimethoxysilylpropyl, methoxyethyl, trimethylsilylmethyl, 11-carbomethoxyundecyl, trimethoxysilylpropyl, methylthiopropyl, trifluoromethyl, 6,6,6-trifluorohexyl, triethoxysilylpropyl, tributoxysilylpropyl, dimethoxymethylsilylpropyl, diethoxymethylsilylpropyl, dibutoxymethylsilylpropyl, diisopropoxymethylsilylpropyl, dimethoxysilylpropyl, diethoxysilylpropyl, dibutoxysilylpropyl, diisopropoxysilylpropyl, 2-(oxyethyl hydrogen propanedioate) and trimethylsilylmethyl.

By "aryl" is meant aromatic groups, including aryl and heteroaryl rings, examples being phenyl, naphthyl, pyridyl, pyrimidyl, benzoxoylanthracenyl.

"Substituted aryl" refers to aromatic groups substituted with functional substituents being the same or different and selected, for example, from carboxylic ester, hydroxyl, alkoxy, amino, secondary amino, tertiary amino, trifluoromethyl, perfluoroalkyl and other substituted and unsubstituted alkyl, substituted and unsubstituted aryl, substituted and unsubstituted olefin and halogen.

Acrylate and methacrylate groups that are useful in the present disclosure include methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, glycidyl acrylate, 2-hydroxyethyl acrylate, hydroxypropyl acrylate (all isomers), hydroxybutyl acrylate (all isomers), diethylaminoethyl acrylate, triethyleneglycol acrylate, N-tert-butyl acrylamide, N-n-butyl acrylamide, N-methyl-ol acrylamide, N-ethyl-ol acrylamide, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilyl propyl acrylate, diethoxysilylpropyl acrylate, dibutoxysilylpropyl acrylate, diisopropoxysilylpropyl acrylate, vinyl acetate, styrene, diethylamino styrene, P-methylstyrene, vinyl benzoic acid, vinylbeuzinsulfonic acid, vinyl propionate, vinyl butyrate, vinyl benzoate, vinyl chloride, vinyl fluoride, vinyl bromide, methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha methyl styrene, trimethoxysilylpropyl methacrylate, triethoxysilylpropyl methacrylate, tributoxysilylpropyl methacrylate, dimethoxymethylsilylpropyl methacrylate, diethoxymethyl-silylpropylmethacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, isopropenyl butyrate, isopropenyl acetate, isopropenyl benzoate, isopropenyl chloride, isopropenyl fluoride, isopropenyl bromide, mideitaconic aciditaconic anhydridedimethyl itaconate. methyl itaconate N-tert-butyl methacrylamide, N-n-butyl methacrylamide, N-methyl-ol methacrylamide, N-ethyl-ol methacrylamide, isopropenylbenzoic acid (all isomers), diethylamino alphamethylstyrene (all isomers), para-methyl-alpha-methylstyrene (all isomers), diisopropenylbenzene (all isomers), isopropenylbenzene sulfonic acid (all isomers), methyl 2-hydroxymethylacrylate, ethyl 2-hydroxymethylacrylate, propyl 2-hydroxymethylacrylate (all isomers), butyl 2-hydroxymethylacrylate (all isomers), 2-ethylhexyl 2-hydroxymethylacrylate, isobornyl 2-hydroxymethylacrylate, and TMI® dimethyl Meta-Isopropenylbenzyl Isocyanate.

The structure of two macromonomers bridged by a hydrazine molecule

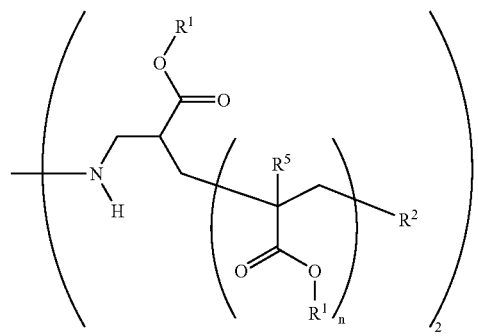

can alternatively be represented in the equivalent form

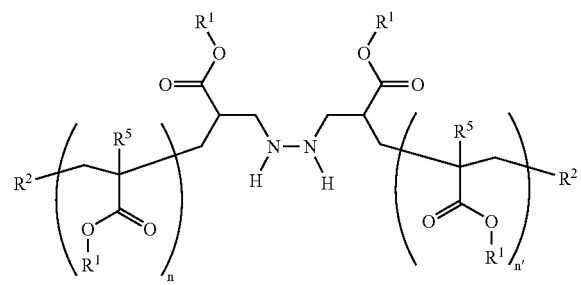

where the value n has become n and n'. This is to make it clear that the two sides of the molecule in the dimeric depiction may be the same or may be different. The statement that each $R^1$ is independently H, alkyl, or aryl, is meant to imply that the macromonomers used to generate the two sides of the molecule may be varied independently. Thus for instance, the left macromonomer may be a low oligomer of methyl methacrylate while the right side of the molecule is generated from a macromonomer that is a random copolymer of butyl methacrylate and hydroxyethyl methacrylate of higher molecular weight. In this example, n and n' would be different, despite the original depiction of the dimeric structure with a single n and the statement that the $R^1$ are each independently varied is indicated by one side of the molecule being all the same while the other side is two alkyls randomly distributed down the chain. Another example would be where the two sides are generated from the same original macromonomer; thus $R^2$ would be the same on both sides and n and n' would be the same. The same random or ordered variation is expected in $R^2$ and $R^5$. Thus, all of the methacrylate structures

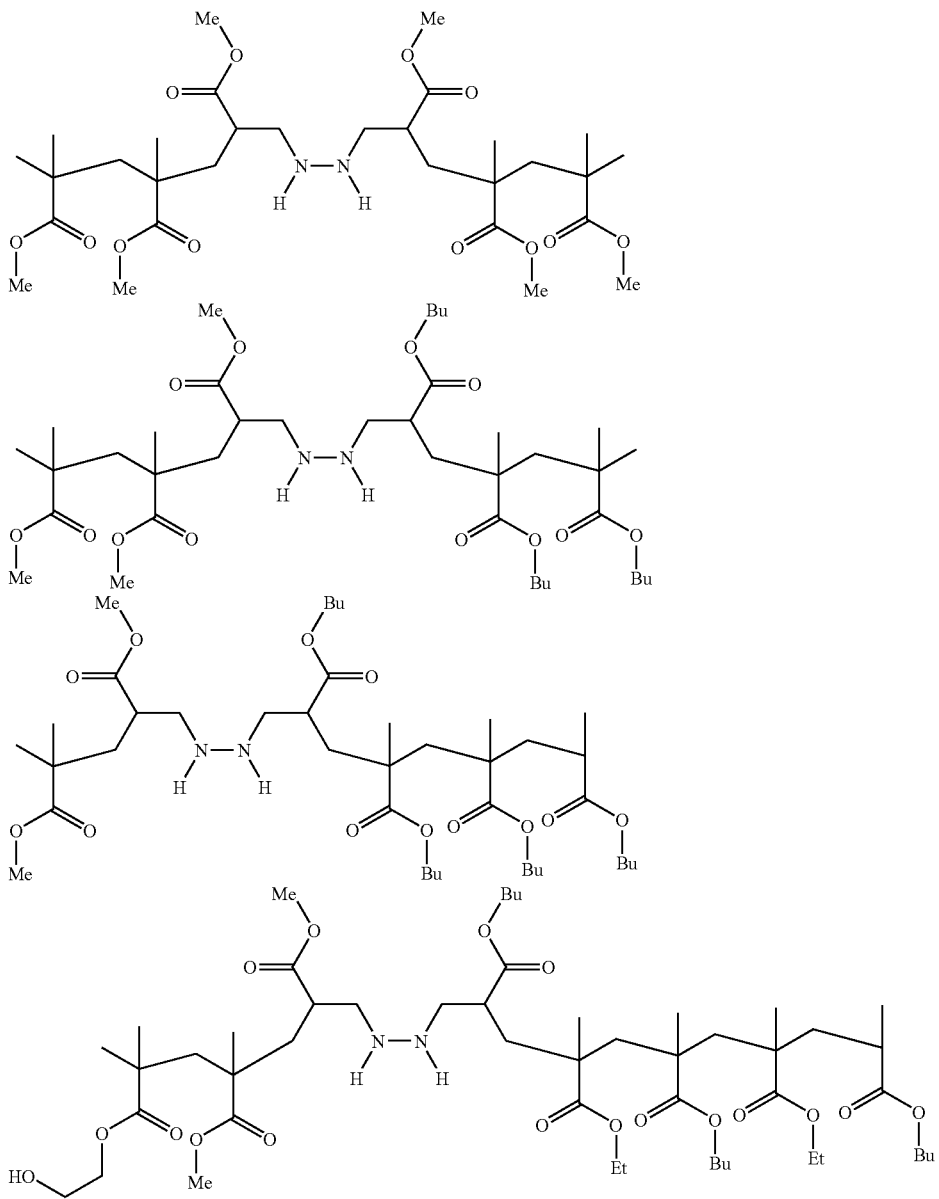

are encompassed within the structure

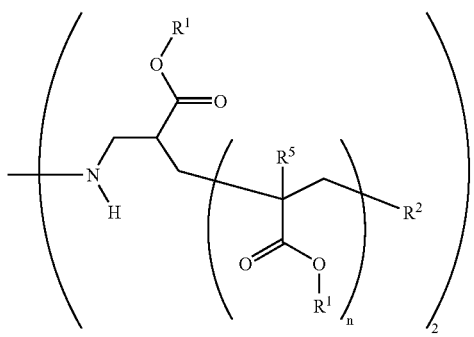

This variability in structure based upon the possible variability in CCT macromonomers is extended to the other representation herein. In the structures above, "Me" represents a methyl group, "Et" represents an ethyl group, and "Bu" represents a butyl group.

The substituent $R^2$ on the oligomer backbone is generally a hydrogen atom, derived from the catalytic chain transfer process, though it is not limited to such. $R^2$ may be selected from alkyls, substituted alkyls, aryls and substituted aryls. $R^2$ may originate from copolymerizations of methacrylic monomers with acrylic monomers, particularly those resulting from cobalt-catalyzed chain transfer as disclosed, for example, in U.S. Pat. No. 6,624,261; from chain initiation with a non-polymerizable monomer as disclosed, for example, in U.S. Pat. No. 6,117,958; or from chain transfer in an acrylic polymerization when methacrylate macromonomers are utilized as chain transfer reagents, as disclosed, for example, in U.S.

Pat. Nos. 5,773,534 and 5,264,530. Finally, $R^2$ may originate from conventional chemical syntheses or modifications.

As used herein, the term "derived from" refers to the origin of substituents ($R^3$ or $R^4$) that are part of the disclosed compositions and that originated from the diverse range of hydrazines that are reacted with the products of catalytic chain transfer. For instance, in a compound derived from the hydrazine

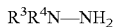

if $R^3$ is octyl, then the substituent octyl is said to have been derived from the organohydrazine, octylhydrazine.

When the macromonomers are synthesized by the copolymerization of acrylates with methacrylates, it is known that the last monomer incorporated will be a methacrylate and the resulting macromonomer will be terminally, olefinically unsaturated, but there is no control over the penultimate monomer, so it may be methacrylate or acrylate. Thus the hydrazine addition further includes the reaction

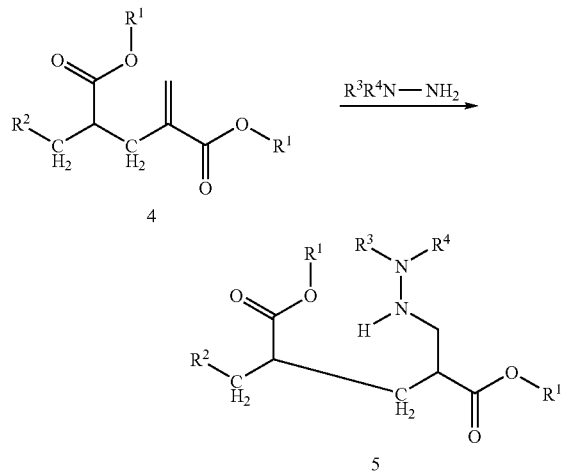

where the substituent $R^2$ may be assumed to incorporate the remainder of the random copolymerization product.

The terminal double bond of oligomers of methacrylonitrile can undergo the amination reaction, just as methacrylates, but the cyclization reaction is not available for these products.

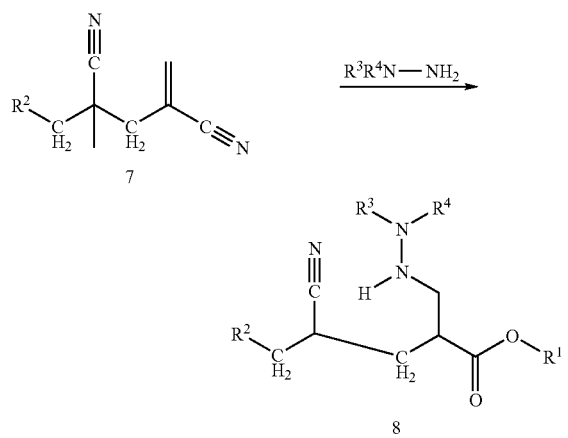

Thus, while 7 is reactive, the reaction is complete with the formation of 8.

The reactions may be carried out in a solvent for convenience, but in general they are desirably carried out with neat reagents. The reactions will take place at room temperature, but it is generally more convenient to carry them out more rapidly at elevated temperatures. As indicated above, the addition can be carried out in the absence of, or in the presence of, any medium or "solvent" that does not otherwise interfere with the reaction. These include alcohols such as isopropanol; amides such as dimethyl formamide; aromatic hydrocarbons such as toluene and xylene; ethers such as tetrahydrofuran and dibutyl ether; ethylene glycol; glycol ethers, alkyl esters or mixed ester ethers such as monoalkyl ether-monoalkanoates. Mixtures of two or more solvents can be used. In general the solvent should have a boiling point higher than the desired reaction temperature so that the reaction may be carried out at elevated temperatures without the need for employing pressure-containing equipment. As used herein, the term "solvent" also refers to media utilized in the preparation of automotive finishes and other paints from the adducts formed according to the processes disclosed herein.

The hydrazine adduct and the ring-closed products are useful in a wide variety of coating and molding applications. Other uses include cast, blown, spun or sprayed applications in fiber, film, sheet, composite materials, inks, paints, and multilayer coatings. They may be utilized in those end-uses as adhesives, adhesion promoters, biological agents, compatibilizers, coupling agents, crosslinkers, curing agents, dispersants, de-foamers, emulsifiers, flocculent, grafting agents, photopolymerizable materials, resists, stabilizers, surface active agents, surfactants, viscosity modifiers, and for other desirable properties. End products taking advantage of available characteristics can include, for example, automotive and architectural coatings or finishes, including high solids, aqueous, or solvent-based finishes.

EXAMPLES

Hydrazine hydrate, N-aminopiperidine, and 2-hydroxyethylhydrazine were purchased from Aldrich Chemical located in St. Louis, Mo. The oligomers of methyl methacrylate were prepared by DuPont at its Marshall Laboratory facility using literature methods. MMA dimer was prepared by running a CCT reaction of methyl methacrylate with a high catalyst loading to synthesize mostly dimer low oligomers and then the purified dimer was distilled from the reaction mixture.

Gas chromatography was carried out on an HP-5890 gas chromatograph (Agilent Technologies, Santa Clara, Calif.) equipped with a flame ionization detector (FID) and autosampler and using a Phenomenex (Phenomenex Inc., Torrance, Calif.) ZB-5 column, 30 m×0.32 mm ID×0.25 micron with a one microliter injection. The GC method was programmed to start at 70° C. for 4 min, followed by temperature ramping to 300° C. at a rate of 10° C./min; the final temperature was held for 17 min. The masses of the various components were determined with an HP-6890 gas chromatograph equipped with an HP-5973 mass selective detector (MSD) and autosampler and using a J&W Scientific DB-5MS column (Agilent Technologies, Santa Clara, Calif.), 30 m×0.25 mm ID×0.25 micron column with a one microliter injection. The GC method was programmed to start at 70° C. for 4 min, followed by temperature ramping to 300° C. at rate of 10° C./min; the final temperature was held for 7 min.

Matrix-Assisted Laser Desorption/Ionization (MALDI) mass spectra were obtained on an Applied Biosystems Voyager DE-STR MALDI mass spectrometer (Applied Biosystems, Foster City, Calif.). Samples were prepared by co-crystallizing the analyte solution with a UV-absorbing matrix (2,5-dihydroxybenzoic acid) onto a stainless steel target plate which was introduced to the mass spectrometer under high vacuum (about 2e-7 torr). Irradiation with a nitrogen laser at 337 nm was used to transfer the analyte to the gas phase, where Na+ or K+ cations ionized the molecules. A voltage of 20 kV was applied to accelerate the ions to determine their mass by time of flight.

The size exclusion chromatography method used to measure the molecular weight distribution in these systems utilized an Alliance 2690 from Waters Corporation (Milford, Mass.), with a Waters 410 refractive index detector (DRI). The software for data reduction was Trisec® Conventional GPC version 3.0 by Viscotek (Viscotek, Houston, Tex.). The columns were two PL Gel Mixed C and one PL Gel 500A columns from Polymer Laboratories (Varian, Inc., Palo Alto, Calif.). The mobile phase was unstabilized THF. Chromatographic conditions were 35° C. at a flow rate of 1.00 ml/min, an injection volume of 100 µL and a run time of 50 min. Samples were dissolved for 4 hours in the mobile phase solvent at RT with moderate agitation. Standards for column n calibration were a set of 10 narrow polydispersity (<1.1) poly(methyl methacrylate) (PMMA) standards with peak molecular weights from 1680 through 1,399,000 available from Polymer Laboratories. The column calibration method with PMMA narrow standards utilized a third order of polynomial fit.

Interaction Polymer Chromatography (IPC) is a new HPLC technique described in several publications (Y. Brun, *The Mechanism of Copolymer Retention Interaction Polymer Chromatography*, J. Liq. Chrom. & Rel. Techniques, 22, 3027, 3067, 1999; Y. Brun, P. Alden, *Gradient Separation of Polymers at Critical Point of Adsorption*, J. Chromatography A, 966 25, 2002). IPC allows one to separate macromolecules by chemical composition and microstructure of polymer chains rather then their size in solution. In case of low MW oligomers (MW about 1000 Da), both, chemical composition and molecular weight affect the retention. The technique was used to analyze obtained reaction mixtures in some of the Examples below.

Example 1

Synthesis of Hydrazine-Terminated Polybutylmethacrylate (PBMA)

PolyBMA obtained by catalytic chain transfer with Mn=2237 was dissolved in THF to achieve a 0.01 mol solution. This solution was mixed with 50 mL of a methanol solution of hydrazine hydrate (0.015 mol). After 10 days at room temperature the reaction was complete. Proton NMR spectra of the product showed <2% of the original vinylic protons of the starting PBMA when compared with the size of the signal from the starting material. The product was

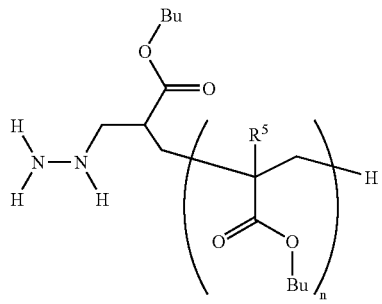

The addition reaction of hydrazine to the double bond of PBMA was confirmed by MALDI mass spectra that showed an increase in mass of 32 Daltons and no unreacted starting PBMA remaining in the product where the accuracy of the analysis for relative concentrations was estimated to be 3%.

Example 2

Synthesis of Poly(butylmethacrylate) Terminated with (2-hydroxyethyl)hydrazine

The reaction was conducted in a manner similar to Example 1 using 2-hydroxyethylhydrazine rather than hydrazine. Both MALDI mass spectroscopy and proton NMR showed <2% of residual vinylic protons. The MALDI signals were shifted by an additional 44 Daltons which corresponds to the difference in masses between hydrazine and hydroxyethylhydrazine, consistent with the structure

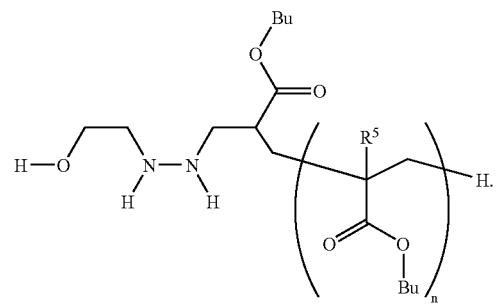

Example 3

Reaction of Hydrazine-Terminated PBMA with Methyl Acrylate

A solution of hydrazine-terminated PBMA from Example 1 was mixed with 4-fold excess of methyl acrylate. After 7 days of standing at room temperature MALDI analysis of the resulting mixture was conducted. More than 85% of original PBMA had reacted with methyl acrylate, giving the product

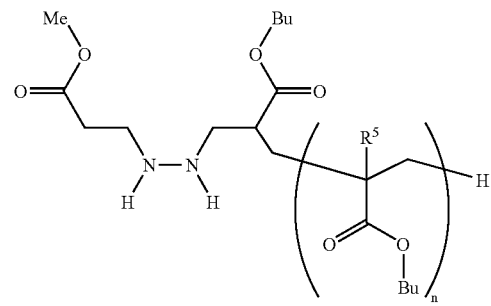

Example 4

Synthesis of PBMA-N$_2$H$_2$-PBMA

The hydrazine-terminated PBMA from Example 1 was mixed in a 1:1 stoichiometry with the same PBMA that was used as the starting material in Example 1 to make the hydrazine-terminated PBMA. This experiment was designed to prove ability of polymethacrylates terminated with hydrazine to add to double bonds of other methacrylates. PBMA identical to that used in the Example 1 was used because diblock methacrylates with different methacrylates provide poorly resolved signals in MALDI.

After 30 days the reaction mixture was analyzed by MALDI. It was found that <15% of the added PBMA has a remaining terminal double bond. The mass spectrum of the mixture was shifter to higher weight, but the MALDI technique does not make it possible to definitively state that the mass was doubled. The resulting product was

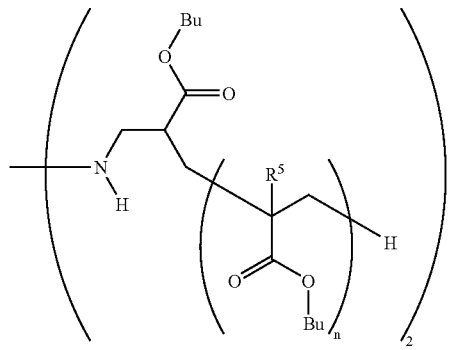

Example 5

Synthesis of PBMA-N$_2$H$_2$-PMMA

Hydrazine-terminated PBMA from Example 1 was mixed with equimolar amount of polyMMA (Mn=2155) in THF. After 45 days at room temperature the sample was analyzed by IPC. It was found that most of the product was the cross-coupled PBMA-N$_2$H$_2$-PMMA copolymer

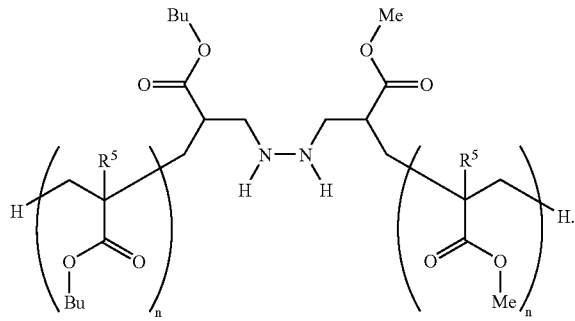

There were also smaller residual unreacted fractions of the starting hydrazine polybutylmethacrylate materials and the PMMA.

Example 6

Synthesis of PBMA-N2H2-P[MMA/HEMA)

Hydrazine-terminated PBMA from Example 1 was mixed with equimolar amount of poly(MMA/HEMA) (Mn=1980; ratio MMA:HEMA=1:1) by IPC. It was found that substantial amount of PBMA-N$_2$H$_2$-P[MMA/HEMA] copolymer had been formed.

Example 7

Synthesis of PBMA-N$_2$H$_2$—CS$_2$-PMMA

Hydrazine-terminated PBMA from Example 1 was mixed with equimolar amount of polyMMA (Mn=2155) and a two-fold molar excess of CS$_2$ in THF. After 7 days at room temperature the sample was analyzed by IPC. It was found that substantial amount of copolymer had formed. Reaction of diblock copolymer formation in the examples 5-8 was monitored by proton NMR as indicated in the Example 2. It was found that without of CS$_2$ reaction completes in 30-40 days while in the presence of CS$_2$ no more than 7 days is required for the same result—disappearance of the vinylic protons. The polymer formed was

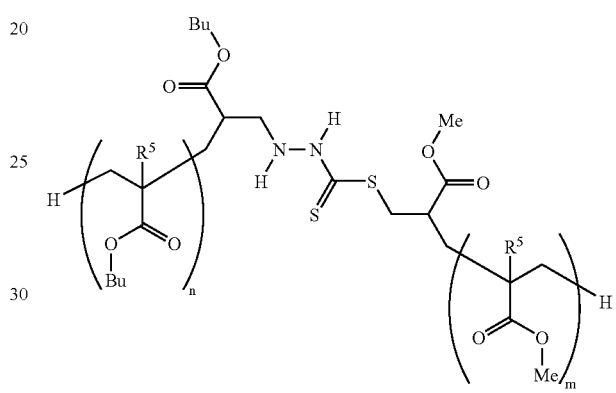

Example 8

Synthesis of PBMA-N$_2$H$_2$—CS$_2$-P[MMA/HEMA)

Hydrazine-terminated PBMA from Example 1 was mixed with equimolar amount of polyMMA/HEMA ((Mn=1980; ration MMA: HEMA=1:1) and two-fold molar excess of CS$_2$ in THF. After 7 days at room temperature the sample was analyzed by IPC. It was found that substantial amount of copolymer formed.

Example 9 Comparative

Attempted Synthesis of PBMA-CS$_2$-P[MMA/HEMA] or PBMA-CS$_2$ or P[MMA/HEMA]-CS$_2$ The same PBMA as was used in reaction with hydrazine in Example 1 was mixed with an equimolar amount of polyMMA (Mn=1980; ratio MMA: HEMA=1:1) and four-fold molar excess of CS$_2$ in THF. Any coupling would have resulted in a statistical mixture of PBMA-CS$_2$-P[MMA/HEMA], PBMA-CS$_2$ and P[MMA/HEMA]-CS$_2$. After 7 days at room temperature the sample was analyzed by NMR. The same amount of vinylic protons was detected as it was before the experiment in the reaction mixture. Hence, CS$_2$ does not react with polymethacrylate in the absence of the hydrazine functionalization.

Example 10

Adduct of MMA Dimer with N-aminopiperidine

Methyl methacrylate dimer (2.00 g, 10 mmol), prepared by distillation from a low molecular weight CCT oligomerization of methyl methacrylate, was weighed into a 20 mL vial. 1-Aminopiperidine, a cyclized 1,1-disubstituted hydrazine, (1.00 g, 10 mmol), was added.

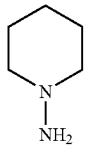

The mixture was shaken giving a homogeneous mixture that turned yellow immediately. The sample was analyzed by gas chromatography and mass spectroscopy A new peak that was the major peak in the GC/MS had a mass of 300 as expected for the adduct

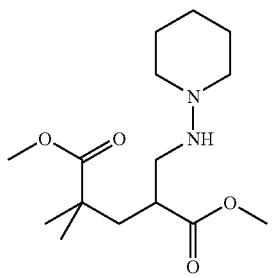

Example 11

Addition of Hydrazine to MMA Dimer

Methyl methacrylate dimer (2.00 g, 10 mmol), prepared by distillation from a low molecular weight CCT oligomerization of methyl methacrylate, was weighed into a 20 mL vial. Hydrazine hydrate(10 mmol), was added. The mixture was shaken giving a homogeneous mixture. The sample was analyzed by GC/MS. Several new peaks evolved with time. The MMA dimer is observed at 11.39 minutes and has a mass of 200. The new peaks appeared at 15.72 and 17.40 seconds. Both had masses of 200, as would be expected for

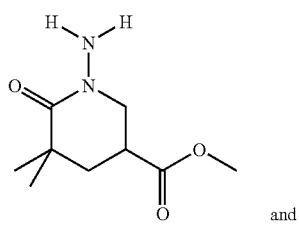

and

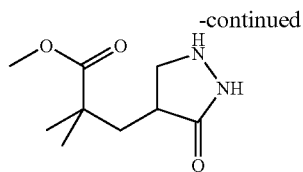

where the additional weight of hydrazine is exactly offset by the loss of methanol. It is recognized that the ester functionalities in methacrylate dimer are more reactive than those in higher oligomers, so these observed cyclization products will be observed less often in higher oligomers.

What is claimed is:

1. A composition having the structure

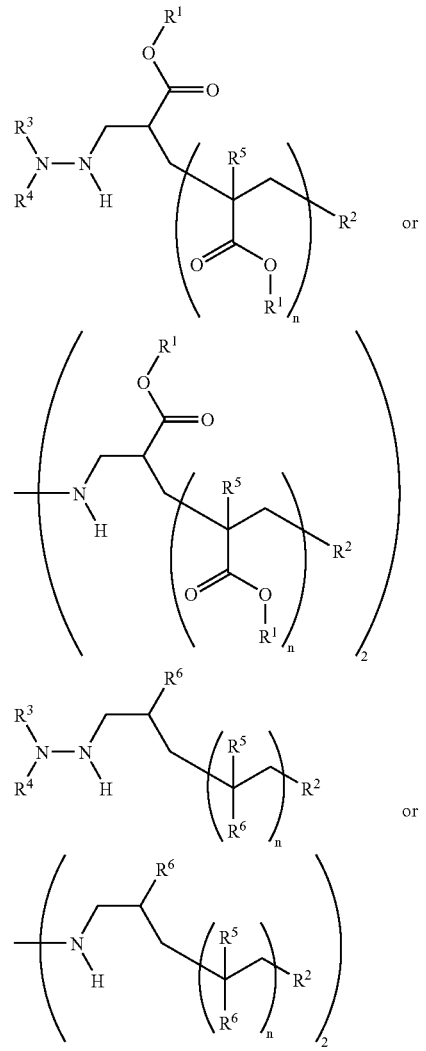

wherein each $R^1$ and $R^2$ are independently H, alkyl of 1-20 carbon atoms, aryl, substituted alkyl of 1-20 carbon atoms, or substituted aryl; $R^3$ and $R^4$ are independently H, alkyl of 1-100 carbon atoms, or substituted alkyl of 1-100 non-hydrogen atoms; $R^5$ is methyl, hydrogen or hydroxymethyl; n=1-100; and $R^6$ are independently —CN, —CO$_2$R$^1$, —COR$^1$, or —CONR$^1$R$^1$.

2. A composition of claim 1, wherein n is from 2 to 20.

3. A composition of claim 1, wherein $R^5$ is methyl.

4. A composition of claim 1, wherein $R^2$ is derived from a macromonomer of an alkyl methacrylate.

5. A product comprising a compound of claim 1, said product selected from the group consisting of inks, dispersions, adhesives, resists, automotive coatings, architectural coatings, paints, and finishes.

6. A product comprising a compound of claim 1, said product selected from the group consisting of dispersants, compatibilizers, adhesives, adhesion promoters, biological agents, compatibilizers, coupling agents, crosslinkers, curing agents, de-foamers, emulsifiers, flocculents, grafting agents, photopolymerizable materials, resists, stabilizers, surface active agents, surfactants, and viscosity modifiers.

* * * * *